United States Patent
Otake et al.

(10) Patent No.: US 6,806,384 B2
(45) Date of Patent: Oct. 19, 2004

(54) PRODUCTION METHOD OF β-AMINO-α-HYDROXYCARBOXYLIC ACID

(75) Inventors: Yasuyuki Otake, Kawasaki (JP); Tomoyuki Onishi, Kawasaki (JP); Sachiko Oka, Kawasaki (JP); Daisuke Takahashi, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 6 days.

(21) Appl. No.: 10/118,958

(22) Filed: Apr. 10, 2002

(65) Prior Publication Data

US 2002/0151722 A1 Oct. 17, 2002

(30) Foreign Application Priority Data

Apr. 11, 2001 (JP) ........................................ 2001-113050
May 16, 2001 (JP) ........................................ 2001-146783

(51) Int. Cl.[7] .......................... C07C 229/00; C07C 59/90
(52) U.S. Cl. ...................... 562/444; 562/555; 562/564
(58) Field of Search ................................ 562/444, 555, 562/564; 560/29, 160

(56) References Cited

U.S. PATENT DOCUMENTS

| | | |
|---|---|---|
| 5,859,248 A | 1/1999 | Kottenhahn et al. |
| 5,919,949 A | 7/1999 | Hilpert |

FOREIGN PATENT DOCUMENTS

| | | |
|---|---|---|
| EP | 0 156 279 | 10/1985 |
| EP | 1 081 133 | 3/2001 |
| EP | 1 148 046 | 10/2001 |
| WO | WO 00/44706 | 8/2000 |

OTHER PUBLICATIONS

Anelli et al, Journal of Organic Chemistry, Fast and Selective Oxidation of Primary Alcohol to Aldehydes or to Carboxylic Acids and of Secondary Alcohols to Ketones Mediated by Oxammonium Salts under Two–Phase Conditions, 1987, 52, pp. 2559–2562.*

B. Munoz, et al., Bioorganic & Medicinal Chemistry, vol. 2, No. 10, pp. 1085–1090, "α–Ketoamide Phe–Pro Isostere as a New Core Structure for the Inhibition of HIV Protease", 1994.

R. Nishizawa, et al., Journal of Medicinal Chemistry, vol. 20, No. 4, pp. 510–515, "Synthesis and Structure–Activity Relationships of Bestatin Analogues, Inhibitors of Aminopeptidase B", 1977.

L. Pegorier, et al., Synlett, pp. 585–586, "Stereocontroled synthesis of *SYN* and *ANTI* N–Protected 3–Amino–2–Hydroxy Alkanoic Esters from Aminoalkyl Epoxides", Jun. 1996.

S. Romeo, et al., Tetrahedron Letters, vol. 35, No. 28, pp. 4939–4942, "Stereoselective Synthesis of Protected Amino Alkyl Epoxides", 1994.

* cited by examiner

Primary Examiner—Johann Richter
Assistant Examiner—Paul A. Zucker
(74) Attorney, Agent, or Firm—Oblon, Spivak, McClelland, Maier & Neustadt, P.C.

(57) ABSTRACT

The present invention provides a production method of an optically active β-amino-α-hydroxycarboxylic acid, which includes the following steps (a)–(c):

(a) treating an optically active N-carbamate protected β-amino epoxide with an acid to give an optically active 5-hydroxymethyl-2-oxazolidinone;

(b) oxidizing the resulting compound in the presence of 2,2,6,6-tetramethyl-1-piperidinyloxy and hypochlorite to give an optically active 4-benzyl-2-oxo-5-oxazolidinecarboxylic acid; and (c) treating the 4-benzyl-2-oxo-5-oxazolidinecarboxylic acid with a base, and a production method of an optically active N-carbamate protected β-amino-α-hydroxycarboxylic acid which includes protection of the amino group with a carbamate type protecting group. The industrial production method of the present invention can produce these compounds efficiently.

23 Claims, No Drawings

PRODUCTION METHOD OF β-AMINO-α-HYDROXYCARBOXYLIC ACID

TECHNICAL FIELD OF THE INVENTION

The present invention relates to a production method of an optically active β-amino-α-hydroxycarboxylic acid. Additionally, the present invention relates to a production method of an optically active N-carbamate type protected β-amino-α-hydroxycarboxylic acid.

BACKGROUND OF THE INVENTION

β-Amino-α-hydroxycarboxylic acid of the formula (1)

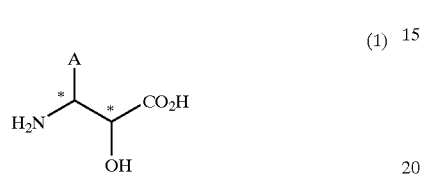
(1)

wherein A is alkyl group having 1 to 10 carbon atoms, aryl group having 6 to 15 carbon atoms or aralkyl group having 7 to 20 carbon atoms, each optionally having substituent(s) and optionally having heteroatom(s) in the carbon skeleton, and * shows an asymmetric carbon atom, is known to be useful as an intermediate for HIV protease inhibitors, carcinostatics and the like (see, for example, B. Munoz et al., Bioorg. Med. Chem., 1994, 2 (10), 1085, R. Nishizawa et al., J. Med. Chem., 1977, 20 (4), 510).

Furthermore, as the production method of β-amino-α-hydroxycarboxylic acid of the formula (1), for example, a production method shown by Scheme 1 in J. Med. Chem., 1977, 20 (4), 510 is known.

Scheme 1

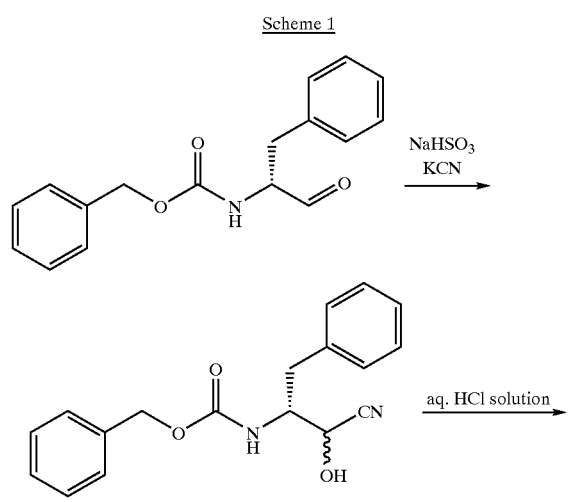

According to the above-mentioned method, however, highly toxic potassium prussiate needs to be used. Moreover, this method shows poor stereoselectivity, and the β-amino-α-hydroxycarboxylic acid is obtained as a diastereomeric mixture. Accordingly, this method is not necessarily an industrially suitable production method.

As a production method of β-amino-α-hydroxycarboxylic acid derivative, moreover, a production method shown by Scheme 2 in Synlett, 1996, 6, 585 is known.

Scheme 2

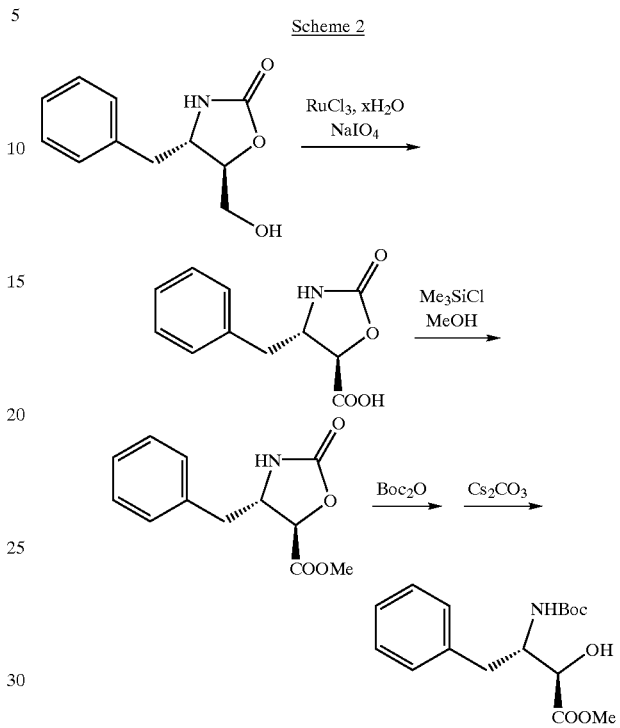

The above-mentioned method requires expensive ruthenium catalyst, caesium carbonate, and also explosive sodium periodate. Accordingly, this production method is not necessarily an industrially suitable production method.

SUMMARY OF THE INVENTION

Accordingly, the present invention aims at providing industrial methods of producing an optically active β-amino-α-hydroxycarboxylic acid and an optically active N-carbamate type protected β-amino-α-hydroxycarboxylic acid.

The present inventors have intensively studied in an attempt to solve the aforementioned problems and obtained a specific β-amino-α-hydroxycarboxylic acid by reacting an N-carbamate type protected β-aminoepoxide with an acid to give specific 5-hydroxymethyl-oxazolidin-2-one, which is oxidized in the presence of 2,2,6,6-tetramethyl-1-piperidinyloxy (hereinafter sometimes to be abbreviated as TEMPO) and hypochlorite to give a specific 2-oxo-5-oxazolidinecarboxylic acid, which is then reacted with a base. Furthermore, they have found that a series of reactions proceed stereoselectively to produce the objective compound having a high optical purity in a high yield.

The present invention is based on such findings and provides the following.

A production method of β-amino-α-hydroxycarboxylic acid of the formula (1)

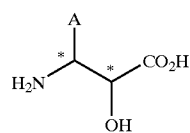

(1)

wherein A is an alkyl group having 1 to 10 carbon atoms, an aryl group having 6 to 15 carbon atoms or an aralkyl group having 7 to 20 carbon atoms, each optionally having substituent(s) and optionally having heteroatom(s) in the carbon skeleton, and * shows an asymmetric carbon atom, provided that, when the configuration of the 2-position and 3-position of β-amino-α-hydroxycarboxylic acid of the formula (1) is (2R,3S), (2S,3R), (2S,3S) or (2R,3R), the configuration of the 2-position and 3-position of N-carbamate protected β-aminoepoxide of the following formula (2) is (2S,3S), (2R,3R) (2R,3S) or (2S,3R), respectively, the configuration of the 4-position and 5-position of the oxazolidin-2-one derivative of the following formula (3) is (4S, 5R), (4R, 5S), (4S, 5S) or (4R, 5R) respectively, and the configuration of the 4-position and 5-position of oxazolidin-2-one derivative of the following formula (4) is (4S, 5R), (4R, 5S), (4S, 5S) or (4R, 5R), respectively: which method comprises the following steps (a)–(c)

(a) treating an N-carbamate protected β-aminoepoxide of the formula (2)

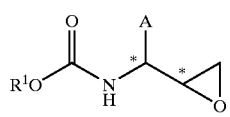

(2)

wherein $R^1$ is a tert-butyl group or a benzyl group, and A and * are as defined above, with an acid to give an oxazolidin-2-one derivative of the formula (3)

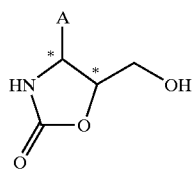

(3)

wherein A and * are as defined above, (b) oxidizing the oxazolidin-2-one derivative of the formula (3) in the presence of 2,2,6,6-tetramethyl-1-piperidinyloxy and hypochlorite to give an oxazolidin-2-one derivative of the formula (4)

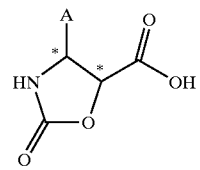

(4)

wherein A and * are as defined above, (c) treating the oxazolidin-2-one derivative of the formula (4) with a base to give the β-amino-α-hydroxycarboxylic acid of the formula (1).

A production method of an N-carbamate protected β-amino-α-hydroxycarboxylic acid of the formula (5)

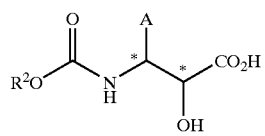

(5)

wherein $R^2$ is a lower alkyl group, a benzyl group or a fluorenylmethyl group, * shows an asymmetric carbon atom and A is as defined above, which method comprises obtaining β-amino-α-hydroxycarboxylic acid of the formula (1) according to the above-mentioned production method, and protecting an amino group of the β-amino-α-hydroxycarboxylic acid with a carbamate type protecting group, provided that when the configuration of the 2-position and 3-position of the β-amino-α-hydroxycarboxylic acid of the formula (1) is (2R,3S), (2S, 3R), (2S,3S) or (2R,3R), the configuration of the 2-position and 3-position of the N-carbamate protected β-amino-α-hydroxycarboxylic acid of the formula (5) is (2R,3S), (2S, 3R), (2S,3S) or (2R,3R), respectively.

DETAILED DESCRIPTION OF THE INVENTION

The present invention is explained in detail in the following.

In the formulas of the present invention, A is an alkyl group having 1 to 10 carbon atoms, an aryl group having 6 to 15 carbon atoms, an aralkyl group having 7 to 20 carbon atoms, each optionally having substituent(s) and optionally having heteroatom(s) in the carbon skeleton, or a hydrogen atom. When A has a substituent, the substituent is free of any particular limitation as long as it does not adversely affect the reaction in the present invention. For example, alkoxy group (preferably having 1 to 7 carbon atoms), nitro group, alkyl group (preferably having 1 to 7 carbon atoms), halogen group and the like are mentioned.

The group containing a heteroatom (nitrogen, oxygen atom and the like) in the carbon skeleton is exemplified by 4-benzyloxyphenylmethyl group and the like.

Such group can be introduced using an amino acid as a starting material. For example, when A is a methyl group, alanine is used, when it is an isopropyl group, valine is used, when it is a 2-methylpropyl group, leucine is used, when it is a 1-methylpropyl group, isoleucine is used, when it is a benzyl group, phenylalanine is used, when it is a cyclohexylmethyl group, cyclohexylalanine is used, and when it is a phenyl group, phenylglycine is used as a starting material for the introduction.

In addition, A may be a group introduced by the use, as a starting material, of an amino acid having a protected functional group of the side chain of the amino acid, such as 0-benzyl tyrosine and the like.

Furthermore, A is not limited to a group introduced from a starting material derived from a natural amino acid, and may be a group introduced from a starting material derived from a non-natural amino acid (e.g., phenyl group, cyclohexylmethyl group).

A is particularly preferably a benzyl group.

In the formulas of the present invention, $R^1$ is a tert-butyl group or a benzyl group. $R^1$ is particularly preferably a tert-butyl group.

In the formulas of the present invention, $R^2$ is a lower alkyl group, a benzyl group or a fluorenylmethyl group. The lower alkyl group is an alkyl group having 1 to 8 carbon atoms, preferably an alkyl group having 1 to 4 carbon atoms. For example, methyl group, ethyl group, tert-butyl group and the like are mentioned. $R^2$ is particularly preferably a tert-butyl group.

The N-carbamate type protected β-aminoepoxide of the formula (2) used as a starting material in the present invention is a known compound and can be produced by a known method comprising, for example, reducing N-carbamate type protected a-chloromethyl ketone of the formula (6), and treating with a base, and the like (see, for example, WO00/44706, EP 1081133).

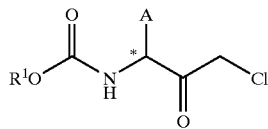

(6)

wherein A is an alkyl group having 1 to 10 carbon atoms, an aryl group having 6 to 15 carbon atoms or an aralkyl group having 7 to 20 carbon atoms, each optionally having substituent(s) and optionally having heteroatom(s) in the carbon skeleton, $R^1$ is a tert-butyl group or a benzyl group, and * shows an asymmetric carbon atom.

The production method of the 5-hydroxymethyl-oxazolidin-2-one derivative (formula (3)), which comprises reacting an N-carbamate type protected β-aminoepoxide derivative (formula (2)) with an acid, is explained in the following.

As the acid, for example, a solid acid such as acidic ion-exchange resin (ion-exchange resin acid catalyst), acidic alumina (alumina acid catalyst), acidic zeolite (zeolite acid catalyst), acidic clay and the like, Lewis acid such as boron trifluoride-ether complex and the like, hydrochloric acid, sulfuric acid, acetic acid, citric acid, methanesulfonic acid, para-toluenesulfonic acid and the like are mentioned. As the acidic ion-exchange resin, for example, Amberlyst 15 ion-exchange resin (Amberlyst, registered trademark) (Sigma-Aldrich) and the like are mentioned.

When the configuration of the 2-position and 3-position of N-carbamate type protected β-aminoepoxide is (2S,3S) or (2R,3R), a solid acid such as acidic ion-exchange resin (ion-exchange resin acid catalyst), acidic alumina (alumina acid catalyst), acidic zeolite (zeolite acid catalyst), acidic clay and the like, Lewis acid such as boron trifluoride-ether complex and the like, citric acid, methanesulfonic acid and para-toluenesulfonic acid are preferable, and acidic ion-exchange resin and citric acid are particularly preferable.

When the configuration of the 2-position and 3-position of N-carbamate type protected β-aminoepoxide is (2R,3S) or (2S,3R), a solid acid is less likely to cause side reactions, such as acidic ion-exchange resin (ion-exchange resin acid catalyst), acidic alumina (alumina acid catalyst), acidic zeolite (zeolite acidic catalyst), acidic clay and the like, and Lewis acid such as boron trifluoride-ether complex and the like are preferable.

These acids may be used alone or in combination of one or more kinds thereof.

As a reaction solvent when the configuration of the 2-position and 3-position of N-carbamate type protected β-aminoepoxide is (2S,3S) or (2R,3R), protonic solvents such as methanol, ethanol, 1-propanol, 2-propanol, 1-butanol, water and the like, and non-protonic solvents such as acetone, 2-butanone, methylisobutylketone, tetrahydrofuran, 1,4-dioxane, acetonitrile, dichloromethane, toluene and the like are preferably used.

These reaction solvents may be used alone or in combination of one or more kinds thereof.

Particularly, acetonitrile, ethanol or 2-propanol, or a mixed solvent of water and acetonitrile, ethanol or 2-propanol is preferable.

When the configuration of the 2-position and 3-position is (2R,3S) or (2S,3R), a non-protonic solvent, such as acetone, 2-butanone, methylisobutylketone, tetrahydrofuran, 1,4-dioxane, acetonitrile, dichloromethane, toluene and the like, particularly acetonitrile, is preferable. The use of a protonic solvent when the configuration of the 2-position and 3-position is (2R,3S) or (2S,3R) is not preferable, because it causes side reactions.

These reaction solvents may be used alone or in combination of one or more kinds thereof.

While the amount of acid to be used varies depending on the kind of acid and solvent to be used, it is preferably 1–5 equivalents, more preferably 1–2 equivalents, relative to the compound of the formula (2). While the reaction temperature also varies depending on the kind of acid and solvent used, it is generally from −20° C. to 100° C., preferably from 20° C. to 80° C. The reaction temperature may be changed during the reaction. The reaction time is not particularly limited but it is preferably about 10 min to 24 hrs.

The reaction is generally carried out under stirring, and after the completion of the reaction, a base may be added to quench the reaction. Preferable examples of the base include sodium hydroxide, potassium hydroxide, lithium hydroxide, sodium carbonate, potassium carbonate and the like.

Furthermore, by extraction as necessary using a solvent such as dichloromethane, ethyl acetate and the like, and evaporation of the organic solvent(s), 5-hydroxymethyl-oxazolidin-2-one (formula (3)) can be isolated.

The oxidization in the next step may be successively carried out without extraction, or without isolating 5-hydroxymethyl-oxazolidin-2-one. The reaction solvent in this case is acetonitrile, or a mixed solvent of acetonitrile and water is most preferable.

The method for obtaining a 2-oxo-5-oxazolidinecarboxylic acid derivative (formula (4)) by oxidization of 5-hydroxymethyl-oxazolidin-2-one derivative (the formula (3)) in the presence of 2,2,6,6-tetramethyl-1-piperidinyloxy and hypochlorite is explained next in the following.

As the solvent, for example, a mixed solvent of a non-protonic solvent such as acetonitrile, dichloromethane, 1,2-dichloroethane and the like and an aqueous solution is preferably used. In this case, more than one kind of non-protonic solvents may be used in a mixture. The ratio of the non-protonic solvent:aqueous solution is preferably 1:4–20:1.

The aqueous solution to be used in admixture with the non-protonic solvent is preferably pH buffer. The reaction mixture generally has pH 7.0–11.0, particularly preferably 8.0–11.0. The buffer is, for example, sodium phosphate buffer, potassium phosphate buffer, sodium carbonate buffer, potassium carbonate buffer and the like. Sodium carbonate buffer is particularly preferable.

The amount of 2,2,6,6-tetramethyl-1-piperidinyloxy to be used is generally 0.001–0.1 equivalent, preferably 0.001–0.01 equivalent, relative to the compound of the formula (3).

As the hypochlorite, sodium hypochlorite, potassium hypochlorite and the like are mentioned, with particular preference given to sodium hypochlorite.

The amount of hypochlorite to be used is generally 2.0–6.0 equivalents, preferably 2.0–2.5 equivalents, relative to the compound of the formula (3). Hypochlorite may be added at once but it is preferably added dropwise slowly.

Where necessary, potassium bromide, sodium bromide and the like may be added before adding hypochlorite. In this case, the amount of potassium bromide to be used is preferably 0.2–2.5 equivalents relative to the compound of the formula (3). Where necessary, chlorite such as sodium chlorite and the like may be added. In this case, the amount of chlorite to be used is preferably 1.0–2.5 equivalents relative to the compound of the formula (3).

The reaction is generally carried out under stirring and after the completion of the reaction, excess hypochlorite is reduced. As the reductant, for example, sodium thiosulfate, sodium hydrogensulfite and the like are used. The reaction temperature is generally preferably from −10° C. to 40° C., particularly preferably from −10° C. to 20° C. The reaction temperature may be changed during reaction. The reaction time is not particularly limited, but it is preferably about 30 min to 24 hrs. after the completion of the dropwise addition.

After adding a reductant, an acid may be added as necessary to adjust the reaction mixture to pH 1.0–4.0 to facilitate the extraction with a solvent such as dichloromethane, ethyl acetate and the like. The acid to be used, for example, hydrochloric acid, sulfuric acid, methanesulfonic acid, para-toluenesulfonic acid and the like are preferably used. After the extraction, the solvent is evaporated to isolate a 2-oxo-5-oxazolidinecarboxylic acid derivative (formula (4)).

Alternatively, the next step for obtaining β-amino-α-hydroxycarboxylic acid (formula (1)) may be successively carried out without extraction, or without isolation of a 2-oxo-5-oxazolidinecarboxylic acid derivative (formula (4)). The solvent to be used in this case is most preferably a mixed solvent of acetonitrile and water.

In the following, a method for obtaining a β-amino-α-hydroxycarboxylic acid derivative (formula (1)) by treating 2-oxo-5-oxazolidinecarboxylic acid derivative (the formula (4)) with a base is explained.

As the base, for example, lithium hydroxide, potassium hydroxide, sodium hydroxide and caesium carbonate, particularly lithium hydroxide and potassium hydroxide, are preferably used.

These bases may be used alone or in combination of one or more kinds thereof.

As the reaction solvent, for example, protonic solvents such as methanol, ethanol, 1-propanol, 2-propanol, 1-butanol, water and the like, or non-protonic solvents such as acetone, 2-butanone, methylisobutylketone, tetrahydrofuran, 1,4-dioxane, acetonitrile and the like are mentioned.

These solvents may be used alone or in combination of one or more kinds thereof.

Particularly, 2-propanol or a mixed solvent of acetonitrile and water is preferable.

While the amount of the base to be used varies depending on the kind of base and solvent, it is generally 1–10 equivalents, more preferably 1–5 equivalents, relative to the compound of the formula (4). While the reaction temperature also varies depending on the kind of base and solvent used, it is generally from −10° C. to 110° C., preferably from 20° C. to 100° C. The reaction temperature may be changed during the reaction. The reaction time is not particularly limited but it is preferably about 30 min to 24 hrs.

The reaction is generally carried out under stirring, and after the completion of the reaction, an acid may be added for crystallization under neutral conditions. The pH in this case is preferably 5.0–8.0, particularly preferably 5.0–7.0. The temperature during crystallization is preferably −10° C. to 30° C., particularly −10° C. to 20° C. The acid to be used is, for example, hydrochloric acid, sulfuric acid, acetic acid and citric acid, particularly hydrochloric acid, are preferable.

In addition, a step for obtaining an N-carbamate type protected β-amino-α-hydroxycarboxylic acid derivative (formula (5)) may be successively carried out without crystallization or isolation of β-amino-α-hydroxycarboxylic acid derivative (formula (1)). In this case, the solvent to be used is particularly preferably acetonitrile, or a mixed solvent of acetonitrile and water.

The method for obtaining an N-carbamate type protected β-amino-α-hydroxycarboxylic acid derivative (formula (5)) is explained in the following, wherein an amino group of β-amino-α-hydroxycarboxylic acid derivative (formula (1)) is protected with a carbamate type protecting group.

It is preferable to adjust the pH in the reaction system to 6–11, particularly 8–10.

As the base to adjust pH, lithium hydroxide, potassium hydroxide, sodium hydroxide, sodium carbonate, potassium carbonate, sodium hydrogencarbonate, potassium hydrogencarbonate and triethylamine are preferably used. Alternatively, hydrochloric acid, sulfuric acid, acetic acid and citric acid are preferably used as an acid to adjust pH.

As the reaction solvent, protonic solvent such as methanol, ethanol, 1-propanol, 2-propanol, 2-butanol, 1-butanol, water and the like, or non-protonic solvent such as acetone, 2-butanone, methylisobutylketone, toluene, dichloromethane, tetrahydrofuran, 1,4-dioxane, acetonitrile and the like are used.

These reaction solvents may be used alone or in combination of one or more kinds thereof.

Particularly, 2-propanol or a mixed solvent of acetonitrile and water is most preferable.

The reaction is generally carried out under stirring. The reaction temperature is generally from 20° C. to 40° C. The reaction time is not particularly limited, but it is preferably about 10 min to 24 hrs.

After the completion of the reaction, pH is adjusted to 1.0–3.0 and the mixture is extracted with a solvent such as ethyl acetate, dichloromethane and the like to give a solution of N-carbamate type protected β-amino-α-hydroxycarboxylic acid.

Where necessary, moreover, the solution is concentrated, a poor solvent, such as hexane, heptane, aqueous lower alcohol solution, water and the like, is added, and crystallization yields N-carbamate type protected β-amino-α-hydroxycarboxylic acid.

Inasmuch as the series of reactions explained above proceed stereoselectively, the objective compound having high optical purity can be obtained in a high yield. A series of reaction schemes when the configuration of the 2-position and 3-position of N-carbamate protected β-aminoepoxide of the formula (2) is (2S,3S) and (2R,3S) are exemplarily shown in the following.

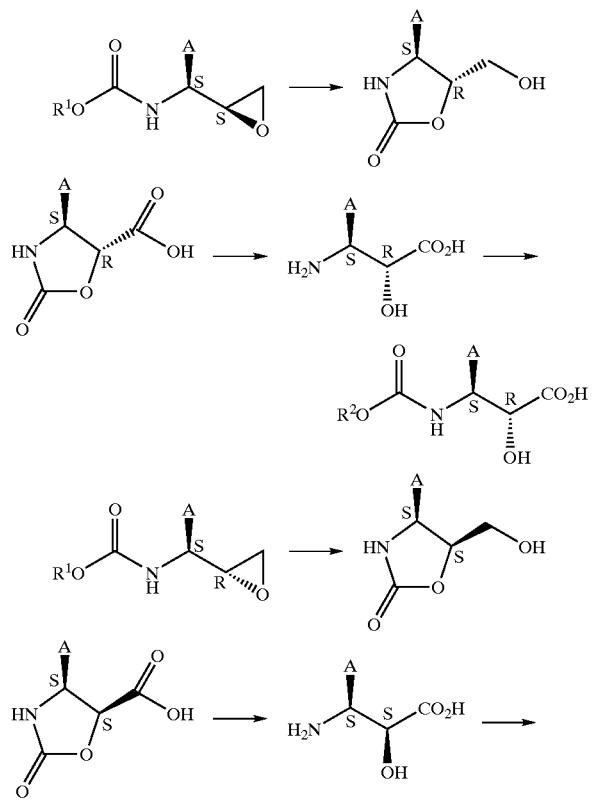

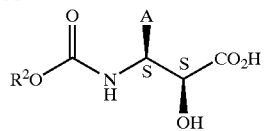

wherein A is an alkyl group having 1 to 10 carbon atoms, an aryl group having 6 to 15 carbon atoms or an aralkyl group having 7 to 20 carbon atoms, each optionally having substituent(s) and optionally having heteroatom(s) in the carbon skeleton, $R^1$ is a tert-butyl group or a benzyl group, * shows an asymmetric carbon atom, and $R^2$ is a lower alkyl group, a benzyl group or a fluorenylmethyl group.

For a series of steps to obtain oxazolidin-2-one derivative (formula (4)) from N-carbamate protected β-aminoepoxide (formula (2)), or N-carbamate type protected β-amino-α-hydroxycarboxylic acid derivative (formula (5)) from N-carbamate protected β-aminoepoxide (formula (2)), for example, a solvent commonly used for each step, such as acetonitrile, a mixed solvent of acetonitrile and water and the like, are used, whereby each product can be subjected to successive reactions without isolation. Accordingly, the process is industrially extremely efficient.

The present invention is explained in more detail by the following Examples, which are not to be construed as limitative.

REFERENCE EXAMPLE 1

Production Method of (2S,3S)-3-tert-butoxycarbonylamino-1-chloro-2-hydroxy-4-phenylbutane To (3S)-3-tert-butoxycarbonylamino-1-chloro-4-phenyl-2-butanone (2.08 g) were added toluene (4.2 ml) and ethanol (16.7 ml). Sodium borohydride (133 mg) was added by portions at −10° C. and the mixture was stirred for 1 hr and 40 min. The reaction was quenched by adding acetic acid (0.40 ml). The reaction mixture was warmed to 60° C. over 1 hr and further stirred 60° C. for 30 min. The reaction mixture was then cooled to −10° C. over 1 hr and 50 min and further stirred at −10° C. for 6 hr. The obtained crystals were collected by filtration, washed with toluene (10.4 ml) and water of 0° C., and dried under reduced pressure to give the objective (2S,3S)-3-tert-butoxycarbonylamino-1-chloro-2-hydroxy-4-phenylbutane (1.52 g, yield 83%). The obtained dry crystals were analyzed by HPLC and found to be (2S,3S):(2R,3S)=99.2:0.8 crystals.

REFERENCE EXAMPLE 2

Production of (2S,3S)-3-tert-butoxycarbonylamino-1,2-epoxy-4-phenylbutane

To (2S,3S)-3-tert-butoxycarbonylamino-1-chloro-2-hydroxy-4-phenylbutane (100 g, (2S,3S):(2R,3S)=99.2:0.8) obtained in the same manner as in Reference Example 1 were added 2-propanol (500 ml) and water (42 ml). 4N Aqueous sodium hydroxide solution (125 ml) was then added thereto, and the mixture was stirred at 4° C. for 3 hr. After the completion of the reaction, citric acid (10.7 g) dissolved in water (583 ml) was added. The reaction mixture was once heated to 27° C., and then cooled to −10° C. over 5 hr. After stirring at −10° C. for 10 hr, the obtained crystals were collected by filtration. The wet crystals were analyzed by HPLC, and as a result, it was confirmed that (2S,3S)-3-tert-butoxycarbonylamino-1,2-epoxy-4-phenylbutane (84.4 g, yield 96%, (2S,3S):(2R,3S)=100:0) was obtained.

EXAMPLE 1

Production of (4S,5R)-4-benzyl-5-hydroxymethyloxazolidin-2-one

To (2S,3S)-3-tert-butoxycarbonylamino-1,2-epoxy-4-phenylbutane obtained in the same manner as in Reference Example 2 (2.75 g) was added ethanol (27.5 ml). 6.8% Aqueous citric acid solution (29.5 g) was then added thereto, and the mixture was stirred at 70° C. for 2 hr. After cooling to room temperature, ethanol was removed under reduced pressure. The residue was extracted with ethyl acetate, dried over anhydrous sodium sulfate and concentrated under reduced pressure. Further, a mixed solvent of hexane (2.5 ml) and ethyl acetate (2.5 ml) was added to allow precipitation of the crystals. The crystals were collected by filtration and washed twice with a mixed solvent of hexane/ethyl acetate (1/1). The obtained crystals were dried to give the objective (4S,5R)-4-benzyl-5-hydroxymethyloxazolidin-2-one (1.79 g) in a yield of 80%.

$^1$H-NMR (DMSO-$d_6$, 300 MHz) δ ppm: 2.73–2.86 (m, 2H), 3.20 (dt, J=12.3, 5.1 Hz, 1H), 3.30–3.41 (m, 1H), 3.80 (ddd, J=5.7, 5.7, 5.7 Hz, 1H), 4.13–4.18 (ddd, J=5.7, 5.7, 5.7 Hz, 1H), 5.01 (dd, J=5.7, 5.7 Hz, 1H), 7.17–7.37 (m, 5H).

$^{13}$C-NMR (DMSO-$d_6$, 300 MHz) δ ppm: 40.4, 54.1, 61.9, 80.5, 126.7, 128.5, 129.7, 136.6, 158.1.

Mass Spectrum m/e: 208 (M+H+).

$[α]D^{20}$=−47.2°(c=1.0, MeOH).

EXAMPLE 2

Production of (4S,5R)-4-benzyl-5-hydroxymethyloxazolidin-2-one

To (2S,3S)-3-tert-butoxycarbonylamino-1,2-epoxy-4-phenylbutane obtained in the same manner as in Reference Example 2 (112 mg) were added toluene (2.24 ml) and p-toluenesulfonic acid monohydrate (81 mg) and the mixture was stirred at 40° C. for 1 hr. The reaction was quenched by adding a saturated aqueous sodium hydrogencarbonate solution, and the reaction mixture was extracted with ethyl acetate. The organic layer was analyzed by HPLC to confirm that (4S,5R)-4-benzyl-5-hydroxymethyloxazolidin-2-one (88.1 mg) was quantitatively obtained.

EXAMPLE 3

Production of (4S,5R)-4-benzyl-5-hydroxymethyloxazolidin-2-one

To wet crystals (37.0 g) containing (2S,3S)-3-tert-butoxycarbonylamino-1,2-epoxy-4-phenylbutane obtained in the same manner as in Reference Example 2 (31.3 g) was added ethanol (300 ml). A solution of citric acid (21.9 g) in water (300 ml) was then added thereto, and the mixture was stirred at 70° C. for 15 hr. The reaction mixture was analyzed by HPLC and confirmed to be (4S,5R)-4-benzyl-5-hydroxymethyloxazolidin-2-one (22.1 g, yield 99%). The reaction mixture was extracted with ethyl acetate (300 ml) and the solvent was removed under reduced pressure. The obtained oil was analyzed by HPLC, and as a result, it was confirmed that (4S,5R)-4-benzyl-5-hydroxymethyloxazolidin-2-one (17.8 g, yield 76%) was obtained.

EXAMPLE 4

Production of (4S,5R)-4-benzyl-2-oxo-5-oxazolidinecarboxylic acid

To (4S,5R)-4-benzyl-5-hydroxymethyloxazolidin-2-one obtained in the same manner as in Example 3 (4.68 g) were added acetonitrile (46.8 ml) and water (46.8 ml), and then sodium hydrogencarbonate (4.68 g), TEMPO (2,2,6,6-tetramethyl-1-piperidinyloxy (0.0468 g) and potassium bromide (2.69 g) were added. The mixture was stirred and 12% aqueous sodium hypochlorite solution (35.0 g) was added dropwise at room temperature over 30 min. The mixture was stirred at room temperature for 7 hr, and 12% aqueous sodium hypochlorite solution (14.0 g) was further added. The mixture was stirred for 12 hr and 12% aqueous sodium hypochlorite solution (7.0 g) was further added, which was followed by stirring for 3 hr. The reaction was quenched by adding sodium hydrogensulfite (2.84 g). The reaction mixture was analyzed by HPLC to confirm that (4S,5R)-4-benzyl-2-oxo-5-oxazolidinecarboxylic acid (4.67 g, yield 93%) was obtained. The mixture was extracted twice with dichloromethane (50 ml, 50 ml) and the solvent of the organic layer was removed under reduced pressure. The obtained oil was analyzed by HPLC to confirm that (4S,5R)-4-benzyl-2-oxo-5-oxazolidinecarboxylic acid (4.00 g, yield 80%) was obtained.

$^1$H-NMR (DMSO-$d_6$, 300 MHz) δ ppm: 2.85 (d,J=6.0 Hz, 2H), 4.01–4.06 (m, 1H), 4.62 (d, J=3.9 Hz, 1H), 7.20–7.36 (m, 5H), 8.03 (S, 1H).

EXAMPLE 5

Production of (2R, 3S)-3-tert-butoxycarbonylamino-2-hydroxy-4-phenylbutyric acid To (4S,5R)-4-benzyl-2-oxo-5-oxazolidinecarboxylic acid obtained in the same manner as in Example 4 (2.39 g) were added 2-propanol (6.7 ml) and 8N aqueous potassium hydroxide solution (6.7 ml), and the mixture was stirred at 90° C. for 3 hr. The mixture was cooled to room temperature and adjusted to pH=8 with 6N aqueous hydrochloric acid solution. To the reaction mixture was added di-tert-butoxycarbonate (2.83 g) dissolved in 2-propanol (6.7 ml) and the mixture was stirred at room temperature for 12 hr. After adjusting the mixture to pH=3, dichloromethane (20 ml) was added to extract the mixture. The solvent of the organic layer was removed under reduced pressure to give crude crystals of (2R,3S)-3-tert-butoxycarbonylamino-2-hydroxy-4-phenylbutyric acid (2.88 g). The crude crystals were analyzed by HPLC to confirm that (2R,3S)-3-tert-butoxycarbonylamino-2-hydroxy-4-phenylbutyric acid (2.55 g, yield 80%) was obtained.

$^1$H-NMR (DMSO-$d_6$, 300 MHz) δ ppm: 1.38 (s, 9H), 2.86–3.02 (m, 2H), 4.06–4.30 (m, 2H), 5.14 (d, J=10.2 Hz, 1H), 7.20–7.35 (m, 1H).

Mass Spectrum m/e: 294.3 (M+H−).

EXAMPLE 6

Production of (2R,3S)-3-amino-2-hydroxy-4-phenylbutyric acid

To (2S,3S)-3-tert-butoxycarbonylamino-1-chloro-2-hydroxy-4-phenylbutane (4.91 g, (2S,3S):(2R,3S)=99.2:0.8) obtained in the same manner as in Reference Example 1 were added 2-propanol (24.6 ml) and water (2.0 ml). 4N Aqueous sodium hydroxide solution (6.1 ml) was then added, and the mixture was stirred at 4° C. for 3 hr. After the completion of the reaction, citric acid (0.525 g) dissolved in water (28.7 ml) was added. The reaction mixture was once heated to 27° C. and cooled to −10° C. over 5 hr. The mixture was stirred at −10° C. for 10 hr, and crystals of (2S,3S)-3-tert-butoxycarbonylamino-1,2-epoxy-4-phenylbutane were collected by filtration. The wet crystals were analyzed by HPLC and found to be (2S,3S):(2R,3S)= 100:0. To the obtained wet crystals was added acetonitrile (3.0 ml) and then a solution of citric acid (3.15 g) in water (2.5 ml) was added. The mixture was stirred at 70° C. for 2 hr. The mixture was cooled to room temperature and adjusted to pH=7.0 with 8N potassium hydroxide solution. To this solution were added sodium hydrogencarbonate (3.44 g), TEMPO (0.0246 g) and potassium bromide (4.88 g) and 12% aqueous sodium hypochlorite solution (25.4 g) was added dropwise at room temperature over 1 hr. After the completion of the dropwise addition, the mixture was stirred for 3 hr and sodium hydrogensulfite (0.853 g) was added to the reaction mixture. To this solution was added 8N aqueous potassium hydroxide solution (8.2 ml) and the mixture was stirred at 90° C. for 18 hr. The reaction mixture was cooled to room temperature and analyzed by HPLC, and as a result, it was confirmed that (2R,3S)-3-amino-2-hydroxy-4-phenylbutyric acid (3.02 g, yield 94%) was obtained. The reaction mixture was then cooled to 0° C. and adjusted to pH=5.5 with 6N aqueous hydrochloric acid solution. The mixture was stirred at 0° C. for 1 hr and the resulting crystals were collected by filtration. The crystals were dried under reduced pressure to give (2R,3S)-3-amino-2-hydroxy-4-phenylbutyric acid as crystals (2.41 g, yield 75%).

EXAMPLE 7

Production of (2R,3S)-3-tert-butoxycarbonylamino-2-hydroxy-4-phenylbutyric acid

To (2S,3S)-3-tert-butoxycarbonylamino-1-chloro-2-hydroxy-4-phenylbutane (22.9 g, (2S,3S):(2R,3S)=99.2:0.8) obtained in the same manner as in Reference Example 1 were added 2-propanol (115 ml) and water (9.6 ml). Furthermore, 4N aqueous sodium hydroxide solution (28.6 ml) was added, and the mixture was stirred at 4° C. for 3 hr. After the completion of the reaction, to the reaction mixture was added citric acid (2.45 g) dissolved in water (134 ml). The reaction mixture was once heated to 27° C. and cooled to -10° C. over 5 hr. The reaction mixture was stirred at -10° C. for 10 hr and crystals of (2S,3S)-3-tert-butoxycarbonylamino-1,2-epoxy-4-phenylbutane were collected by filtration. The wet crystals were analyzed by HPLC and confirmed to be (2S,3S):(2R,3S)=100:0. Acetonitrile (113 ml) was added to the obtained wet crystals, and then a solution of citric acid (14.7 g) in water (56 ml) was added. The mixture was stirred at 70° C. for 2 hr. The reaction mixture was cooled to room temperature and adjusted to pH=7.0 with 8N potassium hydroxide solution. To this solution were added sodium hydrogencarbonate (16.0 g) and TEMPO (0.115 g), and 12% aqueous sodium hypochrolite solution (189 g) was added dropwise at room temperature over 2 hr. After the completion of the dropwise addition, the mixture was stirred for 30 min, and potassium bromide (10.9 g) was added. The mixture was stirred for 13 hr and the 12% aqueous sodium hypochlorite solution (23.6 g) was further added. The mixture was stirred for 1 hr and sodium hydrogensulfite (3.80 g) was added to the reaction mixture. To the solution was added 8N aqueous potassium hydroxide solution (28.6 ml) and the mixture was stirred at 90° C. for 6 hr. The 8N aqueous potassium hydroxide solution (9.6 ml) was further added, and the mixture was stirred at 90° C. for 16 hr. The reaction mixture was cooled to room temperature and adjusted to pH=10 with 6N aqueous hydrochloric acid solution. A solution of di-tert-butoxycarbonate (16.7 g) in acetonitrile (20 ml) was added and the mixture was stirred at 40° C. for 2 hr. The reaction mixture was adjusted to pH=2.0 with 6N aqueous hydrochloric acid solution and the organic layer and aqueous layer were partitioned. The aqueous layer was extracted twice with ethyl acetate (100 ml, 50 ml) and the ethyl acetate layer and the organic layer partitioned earlier were combined. The organic layer was back extracted three times with 1N aqueous sodium hydroxide solution (100 ml, 50 ml, 50 ml). The aqueous layer was then adjusted to pH=1.5 with 6N aqueous hydrochloric acid solution and extracted twice with ethyl acetate (100 ml, 100 ml). This ethyl acetate solution was analyzed by HPLC, and as a result, it was confirmed that (2R,3S)-3-tert-butoxycarbonylamino-2-hydroxy-4-phenylbutyric acid (19.4 g, yield 86%) was obtained. The solvent of this solution was removed under reduced pressure. Methanol (60 ml) and water (60 ml) were added, and while stirring at 0° C., water (90 ml) was added over 30 min. The temperature was once raised to 20° C. and cooled to -3° C. over 2 hr. The mixture was stirred at -3° C. for 2 hr, and the obtained crystals were collected by filtration. The crystals were dried under reduced pressure to give the objective (2R,3S)-3-tert-butoxycarbonylamino-2-hydroxy-4-phenylbutyric acid (16.0 g, yield 71%).

REFERENCE EXAMPLE 3

Production of (2R,3S)-3-tert-butoxycarbonylamino-1-chloro-2-hydroxy-4-phenylbutane Under an argon atmosphere, tri-tert-butoxy lithium aluminum hydride (4.7 g) was added to anhydrous diethyl ether (100 ml). The mixture was cooled to 0° C. and (3S)-3-tert-butoxycarbonylamino-1-chloro-4-phenyl-2-butanone (5.0 g) was added. The mixture was stirred at 0° C. for 3 hr. The reaction was quenched by adding 1N aqueous hydrochloric acid solution (37 ml) to the reaction mixture. The mixture was partitioned and the organic layer was washed with 1N aqueous hydrochloric acid solution and saturated brine. The solvent was evaporated under reduced pressure and the residue was taken up into methanol (23.2 ml) added at room temperature. The obtained solution was analyzed by HPLC, and as a result, it was confirmed that a diastereomeric mixture of 3-tert-butoxycarbonylamino-1-chloro-2-hydroxy-4-phenylbutane was obtained in a total yield of 92.1%. The product ratio of the objective (2R,3S) compound: (2S,3S) compound (diastereomer thereof) was (2R,3S):(2S,3S)=87.4:12.6.

The methanol solution was cooled to 0° C., and water (6 ml) was added. After inoculation of seed crystals, water (22.2 ml) was added dropwise over 1 hr, and the mixture was stirred for 2 hrs. The crystals were collected by filtration, washed twice with heptane (15 ml) and washed twice with water (25 ml). The obtained crystals were dried to give (2R,3S)-3-tert-butoxycarbonylamino-1-chloro-2-hydroxy-4-phenylbutane (4.30 g) in a yield of 85.4%. The product ratio of the objective (2R,3S) compound: (2S,3S) compound (diastereomer thereof) was (2R,3S):(2S,3S)=87.0:13.0.

REFERENCE EXAMPLE 4
Purification of (2R,3S)-3-tert-butoxycarbonylamino-1-chloro-2-hydroxy-4-phenylbutane To (2R,3S)-3-tert-butoxycarbonylamino-1-chloro-2-hydroxy-4-phenylbutane (21.9 g, (2R,3S):(2S,3S)=84.9:15.1) obtained in the same manner as in Reference Example 3 were added 2-propanol (49.2 ml) and water (16.4 ml), and dissolved at 70° C. The solution was cooled to 20° C. over 4 hr. The mixture was stirred at 20° C. for 16 hr, cooled to 15° C. and stirred for 1 hr. The resulting insoluble material was removed by filtration. The obtained filtrate was evaporated to dryness to give (2R,3s)-3-tert-butoxycarbonylamino-1-chloro-2-hydroxy-4-phenylbutane in a yield of 81.9% (17.9 g). The product ratio of the objective (2R,3S) compound: (2S,3S) compound (diastereomer thereof) was (2R,3S):(2S,3S)=98.4:1.6.

$^1$H-NMR (CDCl$_3$, 300 MHz) δ ppm: 1.38 (s, 9H), 2.91 (dd, J=13.2, 8.1 Hz, 1H), 3.01 (dd, J=13.2, 7.1 Hz, 1H), 3.14 (d, J=4.0Hz, 1H), 3.53 (s, 1H), 3.55 (d, J=2.3 Hz, 1H), 3.70–3.77 (m, 1H), 3.79–3.89 (m, 1H), 4.88 (bd, 1H), 7.19–7.35 (m, 5H).

Mass Spectrum m/e:322 (M+Na+).

REFERENCE EXAMPLE 5
Production of (2R,3S)-3-tert-butoxycarbonylamino-1,2-epoxy-4-phenylbutane To (2R,3S)-3-tert-butoxycarbonylamino-1-chloro-2-hydroxy-4-phenylbutane (18.5 g) obtained in the same manner as in Reference Example 4 were added 2-propanol (101.05 ml) and water (33.75 mL) for dissolution and the mixture was cooled to 4° C. To this solution was added NaOH solution (4 mol/L, 25.3 mL) and while maintaining at 4° C., the mixture was stirred for 60 min. By the above operations, a reaction mixture containing (2R,3S)-3-tert-butoxycarbonylamino-1,2-epoxy-4-phenylbutane (15.24 g) was obtained. To this reaction mixture were added citric acid (2.16 g) and water (21.8 mL) while maintaining at 4° C. to neutralize the reaction mixture. Water (20.2 mL) was further added and seed crystals (20 mg) were inoculated and crystal growth was confirmed. After start of crystal growth, the solution was stirred for 1 hr for aging. To the solution was added dropwise water (101 mL) over 1 hr while maintaining at 4° C. The obtained crystals were collected by filtration and wet crystals were dried under reduced pressure at 35° C. to give (2R,3S)-3-tert-butoxycarbonylamino-1,2-epoxy-4-phenylbutane as crystals (14.2 g, yield 93%).

$^1$H-NMR (CDCl$_3$, 300 MHz) δ ppm: 1.38 (s, 9H), 2.59 (bs, 1H), 2.69 (t, J=4.4 Hz, 1H), 2.83–3.04 (m, 3H), 4.12 (bs, 1H), 4.48 (bs, 1H), 7.17–7.37 (m, 5H).

Mass Spectrum m/e:286 (M+Na+).

EXAMPLE 8
Production of (4S,5S)-4-benzyl-5-hydroxymethyloxazolidin-2-one

To dry crystals of (2R,3S)-3-tert-butoxycarbonylamino-1,2-epoxy-4-phenylbutane obtained in the same manner as in Reference Example 5 (1.00 g, (2R,3S):(2S,3S)=98.2:1.8)) was added acetonitrile (3.00 ml), and a boron trifluoride-ether complex (0.539 g) was added. The mixture was stirred at 70° C. for 5 hr. This reaction mixture was analyzed by HPLC, and as a result, it was confirmed that (4S,5S)-4-benzyl-5-hydroxymethloxazolidin-2-one was obtained (0.688 g, yield 87%, (4S,5S):(4S,5R)=98.3:1.7).

EXAMPLE 9
Production of (2S,3S)-3-tert-butoxycarbonylamino-2-hydroxy-4-phenylbutyric acid To dry crystals of (2R,3S)-3-tert-butoxycarbonylamino-1,2-epoxy-4-phenylbutane (18.0 g, (2R,3S):(2S,3S)=98.1:1.9) obtained in the same manner as in Reference Example 5 was added acetonitrile (54.0 ml) and then boron trifluoride-ether complex (8.63 g) was added. The mixture was stirred at 70° C. for 12 hr. The mixture was cooled to room temperature, and water (18 ml) was added. The mixture was then adjusted to pH=7.0 with 8N potassium hydroxide solution and sodium hydrogencarbonate (14.4 g) was added. The mixture was cooled to 0° C. TEMPO (0.103 g) was added, and 12% aqueous sodium hypochlorite solution (106 g) was added dropwise over 1.5 hr. After the completion of the reaction, the mixture was stirred at 0° C. for 3 hr and sodium hydrogensulfite (7.12 g) was added to the reaction mixture. To this solution was added potassium hydroxide (14.8 g) and the mixture was stirred at 50° C. for 17 hr. The reaction mixture was cooled to room temperature and adjusted to pH=10 with 6N aqueous hydrochloric acid solution. A solution of di-tert-butoxycarbonate (23.0 g) in acetonitrile (35.6 ml) was added, and the mixture was stirred at 40° C. for 12 hr while maintaining at pH=10 with 8N aqueous potassium hydroxide solution. The reaction mixture was adjusted to pH=2.0 with 6N aqueous hydrochloric acid solution and the organic layer and aqueous layer were partitioned. The aqueous layer was extracted three times with ethyl acetate (55.0 ml, 27.5 ml, 27.5 ml) and the ethyl acetate layer and the organic layer partitioned earlier were combined. The organic layer was adjusted to pH=10 with 1N aqueous sodium hydroxide solution and back extracted. The resulting organic layer was back extracted with aqueous sodium hydroxide solution (pH=10, 55.0 ml). The two aqueous layers were combined and adjusted to pH=1.7 with 6N aqueous hydrochloric acid solution, and the aqueous layer was extracted twice with ethyl acetate (55.0 ml, 55.0 ml). The solvent of this solution was removed under reduced pressure, and ethyl acetate (81 ml) and hexane (115 ml) were added, dissolved with heating at 65° C. and cooled to 5° C. over 6 hr. The mixture was stirred at 5° C. for 7 hr, and the obtained crystals were collected by filtration. The crystals were dried under reduced pressure to give the objective (2S,3S)-3-tert-butoxycarbonylamino-2-hydroxy-4-phenylbutyric acid (7.89 g, yield 39%). The solvent of the filtrate was then removed under reduced pressure and applied to silica gel column chromatography to give (2S,3S)-3-tert-butoxycarbonylamino-2-hydroxy-4-phenylbutyric acid (4.92 g, yield 24%). In total, 12.8 g of the crystals of (2S,3S)-3-tert-butoxycarbonylamino-2-hydroxy-4-phenylbutyric acid (yield 63%, (2S,3S):(2R,3S)=100:0) was obtained.

$^1$H-NMR (CDCl$_3$, 300 MHz) δ ppm: 1.49 (s, 9H), 2.93–3.04 (m, 2H), 4.15 (ddd, J=10.2, 7.7, 2.2 Hz, 1H), 4.35 (d, J=2.2 Hz, 1H), 4.90 (bs, 1H), 7.20–7.35 (m, 5H).

[α]$D^{20}$=−17.3° (c=1.0, MeOH).

melting point: 143° C.

According to the industrial production method of the present invention, β-amino-α-hydroxycarboxylic acid of the formula (1) (formula (1)), or N-carbamate protected β-amino-α-hydroxycarboxylic acid (formula (5)) having a high optical purity can be produced efficiently.

This application is based on application Nos. 2001-113050 and 2001-146783 filed in Japan, the contents of which are incorporated hereinto by reference.

What is claimed is:

1. A method for producing a β-amino-α-hydroxycarboxylic acid of formula (1)

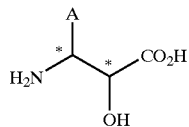

(1)

wherein A is an alkyl group having 1 to 10 carbon atoms, an aryl group having 6 to 15 carbon atoms or an aralkyl group having 7 to 20 carbon atoms, each optionally having substituent(s) and optionally having heteroatom(s) in the carbon skeleton, and * indicates an asymmetric carbon atom, provided that, when the configuration of the 2-position and 3-position of said β-amino-α-hydroxycarboxylic acid of formula (1) is (2R, 3S), (2S,3R), (2S,3S) or (2R,3R), the configuration of the 2-position and 3-position of N-carbamate protected β-aminoepoxide of formula (2) below is (2S,3S), (2R,3R), (2R,3S) or (2S,3R), respectively, the configuration of the 4-position and 5-position of the oxazolidin-2-one compound of formula (3) below is (4S, 5R), (4R,5S), (4S,5S) or (4R,5R) respectively, and the configuration of the 4-position and 5-position of oxazolidin-2-one compound of formula (4) below is (4S,5R), (4R,5S), (4S,5S) or (4R,5R) respectively: said method comprising the following steps (a)–(c)

(a) treating an N-carbamate protected β-aminoepoxide of formula (2)

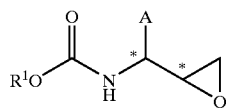

(2)

wherein $R^1$ is a tert-butyl group or a benzyl group, and A and * are as defined above, with an acid to give an oxazolidin-2-one compound of formula (3)

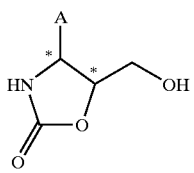

(3)

wherein A and * are as defined above, (b) oxidizing said oxazolidin-2-one compound of formula (3) in the presence of 2,2,6,6-tetramethyl-1-piperidinyloxy and hypochlorite to give an oxazolidin-2-one compound of formula (4)

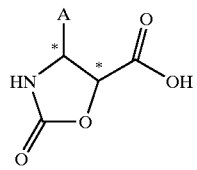

(4)

wherein A and * are as defined above, (c) treating said oxazolidin-2-one compound of formula (4) with a base to give said β-amino-α-hydroxycarboxylic acid of formula (1).

2. The method of claim 1, further comprising a step of crystallizing said β-amino-α-hydroxycarboxylic acid of formula (1).

3. The method according to claim 1 further comprising a method for producing an N-carbamate protected β-amino-α-hydroxycarboxylic acid of formula (5).

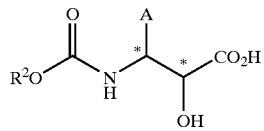

(5)

wherein $R^2$ is a lower alkyl group, a benzyl group or a fluorenylmethyl group, * indicates an asymmetric carbon atom and A is an alkyl group having 1 to 10 carbon atoms, an aryl group having 6 to 15 carbon atoms or an aralkyl group having 7 to 20 carbon atoms, each optionally having substituent(s) and optionally having heteroatom(s) in the carbon skeleton, said method comprising obtaining a βamino-α-hydroxycarboxylic acid of formula (1), and protecting an amino group of said β-amino-α-hydroxycarboxylic acid with a carbamate type protecting group, provided that when the configuration of the 2-position and 3-position of said β-amino-α-hydroxycarboxylic acid of formula (1) is (2R,3S), (2S,3R), (2S,3S) or (2R,3R), the configuration of the 2-position and 3-position of said N-carbamate protected β-amino-α-hydroxycarboxylic acid of formula (5) is (2R,3S), (2S,3R), (2S,3S) or (2R,3R), respectively.

4. The method of claim 1, wherein when A has a substituent, said substituent is selected from the group consisting of an alkoxy group having 1 to 7 carbon atoms, a nitro group, an alkyl group having 1 to 7 carbon atoms, and a halogen.

5. The method of claim 1, wherein A is a group selected from the group consisting of 4-benzyloxyphenylmethyl, methyl, isopropyl, 2-methylpropyl, 1-methylpropyl, benzyl, cyclohexylmethyl, and phenyl.

6. The method of claim 1, wherein A is a benzyl group.

7. The method of claim 1, wherein said acid is selected from the group consisting of acidic ion-exchange resin, acidic alumina, acidic zeolite, acidic clay, boron trifluoride-ether complex, hydrochloric acid, sulfuric acid, acetic acid, citric acid, methanesulfonic acid, and para-toluenesulfonic acid.

8. The method of claim 5, wherein said acid is selected from the group consisting of acidic ion-exchange resin, acidic alumina, acidic zeolite, acidic clay, boron trifluoride-ether complex, hydrochloric acid, sulfuric acid, acetic acid, citric acid, methanesulfonic acid, and para-toluenesulfonic acid.

9. The method of claim 6, wherein said acid is selected from the group consisting of acidic ion-exchange resin, acidic alumina, acidic zeolite, acidic clay, boron trifluoride-ether complex, hydrochloric acid, sulfuric acid, acetic acid, citric acid, methanesulfonic acid, and para-toluenesulfonic acid.

10. The method of claim 1, wherein said hypochlorite is selected from the group consisting of sodium hypochlorite and potassium hypochlorite.

11. The method of claim 5, wherein said hypochlorite is selected from the group consisting of sodium hypochlorite and potassium hypochlorite.

12. The method of claim 6, wherein said hypochlorite is selected from the group consisting of sodium hypochlorite and potassium hypochlorite.

13. The method of claim 1, wherein said base is selected from the group consisting of lithium hydroxide, potassium hydroxide, sodium hydroxide, and cesium carbonate.

14. The method of claim 5, wherein said base is selected from the group consisting of lithium hydroxide, potassium hydroxide, sodium hydroxide, and cesium carbonate.

15. The method of claim 6, wherein said base is selected from the group consisting of lithium hydroxide, potassium hydroxide, sodium hydroxide, and cesium carbonate.

16. The method of claim 3, wherein A is a group selected from the group consisting of 4-benzyloxyphenylmethyl, methyl, isopropyl, 2-methylpropyl, 1-methylpropyl, benzyl, cyclohexylmethyl, and phenyl.

17. The method of claim 16, wherein $R^2$ is a tert-butyl group.

18. The method of claim 3, wherein $R^2$ is a tert-butyl group.

19. The method of claim 3, wherein A is a benzyl group.

20. The method of claim 19, wherein $R^2$ is a tert-butyl group.

21. The method of claim 3, wherein said protecting an amino group of said β-amino-α-hydroxycarboxylic acid of formula (1) with a carbamate type protecting group is carried out by reacting said β-amino-α-hydroxycarboxylic acid with di-tert-butoxycarbonate.

22. The method of claim 16, wherein said protecting an amino group of said β-amino-α-hydroxycarboxylic acid of formula (1) with a carbamate type protecting group is carried out by reacting said β-amino-α-hydroxycarboxylic acid with di-tert-butoxycarbonate.

23. The method of claim 19, wherein said protecting an amino group of said β-amino-α-hydroxycarboxylic acid of formula (1) with a carbamate type protecting group is carried out by reacting said β-amino-α-hydroxycarboxylic acid with di-tert-butoxycarbonate.

* * * * *